(12) United States Patent
Kageyama et al.

(10) Patent No.: US 8,906,641 B2
(45) Date of Patent: Dec. 9, 2014

(54) METHOD FOR MEASURING ANIMAL α-AMYLASE

(75) Inventors: Shigeki Kageyama, Asaka (JP); Nobuhito Masuda, Asaka (JP); Kazuya Kawasaki, Asaka (JP); Satoru Toda, Asaka (JP)

(73) Assignee: FUJIFILM Corporation, Tokyo (JP)

( * ) Notice: Subject to any disclaimer, the term of this patent is extended or adjusted under 35 U.S.C. 154(b) by 371 days.

(21) Appl. No.: 12/015,151

(22) Filed: Jan. 16, 2008

(65) Prior Publication Data

US 2008/0182285 A1 Jul. 31, 2008

(30) Foreign Application Priority Data

Jan. 17, 2007 (JP) ................. 2007-007673

(51) Int. Cl.
*C12Q 1/40* (2006.01)
*G01N 33/52* (2006.01)

(52) U.S. Cl.
CPC .............. *C12Q 1/40* (2013.01); *G01N 33/523* (2013.01); *G01N 33/526* (2013.01)
USPC ........................................................ 435/22

(58) Field of Classification Search
None
See application file for complete search history.

(56) References Cited

U.S. PATENT DOCUMENTS

| | | | |
|---|---|---|---|
| 4,649,108 A | 3/1987 | Blair | |
| 4,709,020 A | 11/1987 | Rauscher et al. | |
| 4,794,078 A * | 12/1988 | Blair | 435/18 |
| 4,818,692 A | 4/1989 | Rauscher et al. | |
| 5,077,011 A * | 12/1991 | Amano et al. | 422/56 |
| 6,387,646 B1 * | 5/2002 | Kimata et al. | 435/22 |
| 2003/0157584 A1 | 8/2003 | Kawasaki et al. | |
| 2003/0175842 A1 * | 9/2003 | Yamaguchi et al. | 435/22 |
| 2008/0050451 A1 * | 2/2008 | Mabry | 424/600 |
| 2009/0324571 A1 * | 12/2009 | Steinberg et al. | 424/94.2 |

FOREIGN PATENT DOCUMENTS

| | | |
|---|---|---|
| EP | 1 342 790 A2 | 9/2003 |
| JP | 61-63299 A | 4/1986 |
| JP | 62-138198 A | 6/1987 |
| JP | 62-51960 B2 | 11/1987 |
| JP | 2-36238 B2 | 8/1990 |
| JP | 5-50274 B2 | 7/1993 |
| JP | 10-14597 A | 1/1998 |
| JP | 2003-210195 A | 7/2003 |

OTHER PUBLICATIONS

Lorentz, "Routine α-Amylase Assay Using Protected 4-Nitrophenyl-1, 4-α-D-maltoheptaoside and a Novel α-Glucosidase," Clinical Chemistry 46, No. 5, 2000, pp. 644-649.
Japanese Office Action for Application No. 2008-007587 dated Aug. 28, 2012 (with English translation).

* cited by examiner

*Primary Examiner* — Lisa J Hobbs
(74) *Attorney, Agent, or Firm* — Birch, Stewart, Kolasch & Birch, LLP

(57) ABSTRACT

It is an object of the present invention to provide a method capable of measuring a high concentration (up to 2500 U/L) of animal sample without dilutions, which is further capable of specifically measuring α-amylase even in a sample comprising animal α-amylase (EC 3.2.1.1) and glucoamylase (EC 3.2.1.3). The present invention provides a method for specifically measuring α-amylase contained in a non-human animal sample comprising α-amylase and glucoamylase without diluting said sample, wherein measurement is carried out by using an oligosaccharide having a protected nonreducing terminus and a p-nitrophenyl group at the reducing terminus thereof, and pH of reaction is 6 or more, and less than 7.

6 Claims, 5 Drawing Sheets

METHOD FOR MEASURING ANIMAL α-AMYLASE

TECHNICAL FIELD

The present invention relates to a method for measuring a specific component contained in a liquid such as the blood of animals.

BACKGROUND ART

Amylase is one type of digestive enzyme. This enzyme hydrolyzes a glycoside bond, so as to digest amylose or amylopectin existing in starch to glucose, maltose, and an oligosaccharide. As such amylase, α-amylase (EC 3.2.1.1), β-amylase (EC 3.2.1.2), and glucoamylase (EC 3.2.1.3) have been known. The α-amylase irregularly cleaves the 1,4-α-bond of starch or glycogen to generate a polysaccharide or an oligosaccharide. The β-amylase decomposes starch or glycogen from the nonreducing terminus of a sugar chain to generate maltose. The glucoamylase decomposes the 1,4-α-bond of the nonreducing terminus of a sugar chain to generate glucose.

As an example of an amylase-measuring method, JP Patent Publication (Kokoku) No. 62-51960 B (1987) describes a method for measuring human α-amylase in a solution using an amylase substrate whose nonreducing terminus has been blocked. In addition, JP Patent Publication Kokoku) No. 2-36238 B (1990) describes an amylase-measuring method using a substrate whose nonreducing terminus is not protected and whose reducing terminus is a carboxylphenyl group. Moreover JP Patent Publication (Kokoku) No. 5-50274 B (1993) describes a method for measuring human α-amylase using a dry analysis element comprising a substrate whose nonreducing terminus is not protected. Furthermore, JP Patent Publication (Kokai) No. 2003-210195 A describes that when α-amylase activity is measured using an α-amylase activity-measuring solution comprising a predetermined concentration of NaCl and a predetermined concentration of $CaCl_2$, the activity of wheat α-amylase whose optimal pH is on the acidic side can be measured with high sensitivity.

DISCLOSURE OF THE INVENTION

It is an object of the present invention to provide a method capable of measuring a high concentration (up to 2500 U/L) of animal sample without dilutions, which is further capable of specifically measuring α-amylase even in a sample comprising animal α-amylase (EC 3.2.1.1) and glucoamylase (EC 3.2.1.3).

The present inventors have conducted intensive studies directed towards achieving the aforementioned object. As a result, in a method using a non-human animal sample comprising α-amylase and glucoamylase without diluting it so as to specifically measure α-amylase contained in the aforementioned sample, the inventors have found that, by adjusting the pH of reaction to an acidic pH, a high concentration of animal sample can be measured without dilutions and α-amylase can be specifically measured even in a sample comprising animal α-amylase and glucoamylase. The present invention has been completed based on such findings.

That is to say, the present invention provides: a method for specifically measuring α-amylase contained in a non-human animal sample comprising α-amylase and glucoamylase without diluting said sample, wherein measurement is carried out by using an oligosaccharide having a protected nonreducing terminus and a p-nitrophenyl group at the reducing terminus thereof, and pH of reaction is 6 or more, and less than 7.

Preferably, the measurement is carried out by using a dry analysis element comprising an oligosaccharide having a protected nonreducing terminus and a p-nitrophenyl group at the reducing terminus thereof and a mordant on an identical or different reagent layer(s) thereof. When the present invention is carried out using a dry analysis element, it is preferred that two reagent layers are provided, namely, a developing reaction layer for spreading a sample and conducting the enzyme reaction of amylase, and a coloring layer comprising a mordant for effectively developing the color of a pigment generated. Such two layers may be unified to form a single layer, or another reagent layer having a different function may also be added thereto.

The oligosaccharide having a protected nonreducing terminus and a p-nitrophenyl group at the reducing terminus thereof is preferably 4,6-ethylidene-4-nitrophenyl-α-D-maltoheptaoside.

The mordant is preferably an organic polymer comprising a quaternary ammonium salt.

The mordant is preferably a latex consisting of poly-co-(styrene-methylmorpholiniummethylstyrene-divinylbenzene).

The pH of the reaction is preferably between pH 6.0 and 6.9.

The pH of the reaction is preferably between pH 6.3 and 6.7.

The α-amylase activity calculation time (window) is preferably 5 minutes or less.

The α-amylase activity calculation time (window) is preferably 1 to 5 minutes

The non-human animal sample is preferably a canine sample or a cat sample.

According to the present invention, a high concentration (up to 2500 U/L) of animal sample can be measured without dilutions, and further, α-amylase can be specifically measured even in a sample comprising animal α-amylase (EC 3.2.1.1) and glucoamylase (EC 3.2.1.3). That is, by the present invention, the previous measurement range of canine amylase that had been up to 1200 U/L was expanded up to 2500 U/L. By achieving the aforementioned performance, a sample with a high amylase value could be measured without complicated dilution operations, and thus the present inventors have succeeded in relieving the bother of users of doing such dilution operations. Moreover, using, as a substrate, an oligosaccharide having a protected nonreducing terminus and a p-nitrophenyl group at the reducing terminus thereof, such as 4,6-ethylidene-4-nitrophenyl-α-D-maltoheptaoside, errors due to glucoamylase contained in a canine sample disappeared, and thus it became possible to carry out an α-amylase-specific measurement.

BEST MODE FOR CARRYING OUT THE INVENTION

Figure 1:
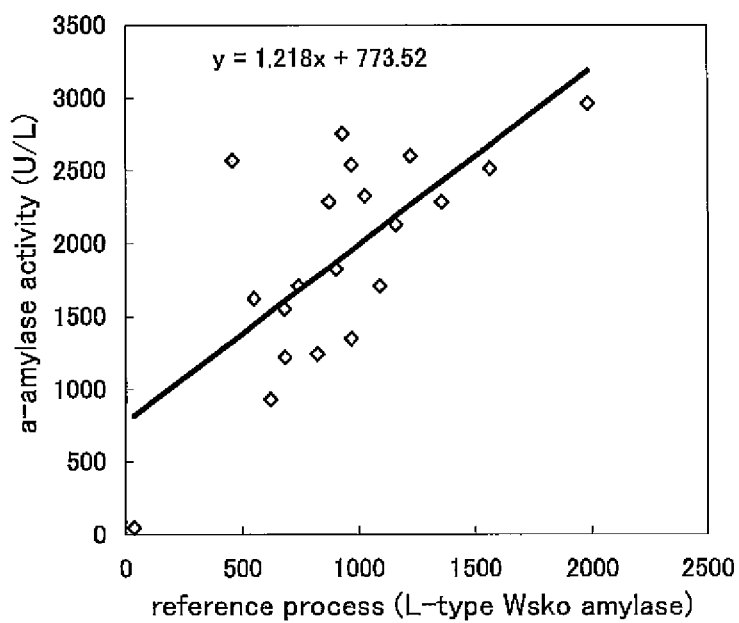
FIG. 1 shows the results obtained by making a 3 times dilution of a canine sample in normal saline, followed by measurement using the dry analysis element produced in Comparative example 1.

The embodiments of the present invention will be specifically described below.

The present invention relates to a method for specifically measuring α-amylase contained in a non-human animal sample comprising α-amylase and glucoamylase without diluting the aforementioned sample, wherein measurement is carried out by using an oligosaccharide having a protected nonreducing terminus and a p-nitrophenyl group at the reducing terminus thereof, and pH of reaction is 6 or more, and less than 7.

The non-human animal sample comprising α-amylase and glucoamylase is not particularly limited. A canine sample which is known to contain more glucoamylase than in human sample can be used. Further, mammal sample such as a cat, a monkey, a mouse, a hamster, a rabbit, a camel, a sheep, a cattle, a buffalo or a swine can also be used. Further, animal sample such as a horse, a goat, an avian, and a reptile can also be used as a sample. Preferably, a sample of canine, cat, monkey, mouse, hamster, or swine can be used. Further preferably, a sample of canine or cat can be used.

Preferably in the present invention, measurement can be carried out by using a dry analysis element comprising an oligosaccharide having a protected nonreducing terminus and a p-nitrophenyl group at the reducing terminus thereof and a mordant on an identical or different reagent layer(s) thereof. An oligosaccharide having a protected nonreducing terminus and a p-nitrophenyl group at the reducing terminus thereof (4,6-ethylidene-4-nitrophenyl-α-D-maltoheptaoside, for example) used as a substrate of α-amylase in the present invention is preferably contained in the developing reaction layer of the dry analysis element.

α-amylase reacts with the aforementioned substrate to generate p-nitrophenol via α-glucosidase so as to develop color. In the acidic pH, ionization of p-nitrophenol is unlikely to occur, and coloring efficiency is worse.

In the present invention, a mordant is contained in the reagent layer of the dry analysis element in order to solve the aforementioned problem. As such a mordant, a cationic organic polymer for binding an acid dye, such as p-nitrophenol used in the present invention, can be used. Examples of such a cationic organic polymer include a polymer comprising a secondary or tertiary amino group and a polymer comprising a quaternary cationic group. Such a polymer has a molecular weight of 5000 to 200000, and particularly preferably a molecular weight of 10000 to 50000. Among such polymers, a polymer that hardly moves from a hydrophilic colloidal layer to another layer is preferable. For example, a polymer that cross-links with a hydrophilic colloid such as gelatin, a water-insoluble cationic polymer, and a water-based sol (or dispersed latex particles) can be preferably used.

Particularly preferred cationic polymers are as described below.

(1) A polymer having a quaternary ammonium group and also having a group capable of covalently binding to gelatin (e.g. an aldehyde group, a chloroalkanoyl group, a chloroalkyl group, a vinylsulfonyl group, a pyridiniumpropionyl group, a vinylcarbonyl group, an alkylsulfonoxy group, etc.), such as the polymer represented by the following formula:

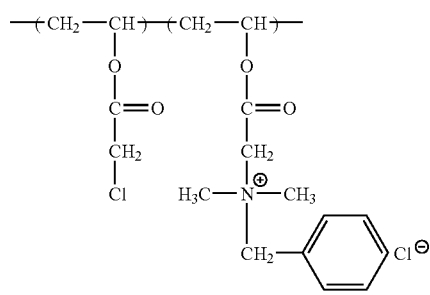

(2) A reaction product generated as a result of the reaction of a copolymer consisting of a repeating unit of the monomer represented by the following formula (I), a repeating unit of another ethylene unsaturated monomer and a repeating unit of another ethylene unsaturated monomer, with a cross-linking agent (e.g. bisalkanesulfonate, bisallenesulfonate, etc.):

[Formula (I)]

$$-(CH-C)-$$
with substituents $R_1$, $R_2$, $Q$, $R_3$, $R_4$, $R_5$, $N^+$, $X^-$ wherein $R_1$ is H or an alkyl group;
$R_2$ is H, an alkyl group, or an aryl group;
Q is a divalent group;
each of $R_3$, $R_4$, and $R_5$ is an alkyl group or an aryl group, or at least two of $R_3$, $R_4$, and $R_5$ may bind to each other to form a hetero ring; and
X is anion,
(wherein the aforementioned alkyl group or aryl group may be optionally substituted).

(3) A polymer represented by the following formula (II):

[Formula (II)]

$$-(A)_x-(B)_y-(CH_2-CH)_z-$$
with phenyl group bearing $CH_2-Q^+-R_2$, $R_1$, $R_3$, $M^-$ wherein x indicates approximately 0.25% to 5% by mole;
y indicates approximately 0% to 90% by mole;
z indicates approximately 10% to 99% by mole;
A is a monomer having at least two ethylene unsaturated bonds;
B is a copolymerizable ethylene unsaturated monomer;
Q is N or P; and
each of $R_1$, $R_2$, and $R_3$ is an alkyl group or a cyclic hydrocarbon group, or at least two of $R_1$, $R_2$, and $R_3$ may bind to each other to form a ring,
(wherein such groups or rings may be substituted).

(4) A copolymer consisting of (a) represented by the following formula (III), (b), and (c):

(a)

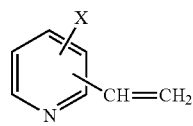 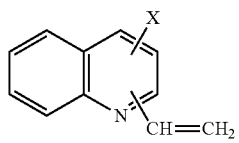

[Formula (III)]

wherein X is a hydrogen atom, an alkyl group, or a halogen atom (wherein the alkyl group may be optionally substituted);
(b) an acrylic ester; and
(c) acrylonitrile.
(5) A water-insoluble polymer having one-third or more of a repeating unit represented by the following formula (IV):

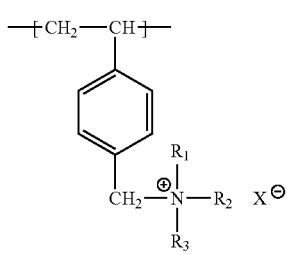

[Formula (IV)]

wherein each of $R_1$, $R_2$, and $R_3$ represents an alkyl group, and the total number of carbon atoms of $R_1$ to $R_3$ is 12 or greater (wherein the alkyl group may be substituted); and
X is anion.

Among such mordants, a latex consisting of poly-co-(styrene-methylmorpholiniummethylstyrene-divinylbenzene) is particularly preferable.

The pH of the reaction in the present invention is an acidic pH, specifically 6.0 or more and less than 7, preferably between pH 6.0 and 6.9, and particularly preferably between pH 6.3 and 6.7.

A dry analysis element is used as an analysis element in the measurement method of the present invention. An example of such a dry analysis element that can be used in the present invention is an analysis element, which comprises at least a layer comprising an oligosaccharide substrate labeled with p-nitrophenol and a layer comprising α-glucosidase on a supporting medium thereof (hereinafter, such layers may be referred to as reagent layers, at times). It may also be possible that such an oligosaccharide substrate labeled with p-nitrophenol and α-glucosidase be contained in a single reagent layer. Moreover, a water absorption layer or the like may also be established between such a supporting medium and the aforementioned reagent layer, as desired.

As a supporting medium that can be used in the present invention, all of a light-nonpermeable (non-transparent) supporting medium, a light-semipermeable (semi-transparent) supporting medium, and a light-permeable (transparent) supporting medium can be used. In general, a light-permeable, water-nonpermeable supporting medium is preferable. Preferred materials for such a light-permeable, water-nonpermeable supporting medium include polyethylene terephthalate and polystyrene. For strong adhesion of a hydrophilic layer, a supporting medium, which comprises an undercoating layer or which has been subjected to a hydrophilic treatment, is preferably used.

A developing reaction layer contains an oligosaccharide substrate labeled with p-nitrophenol and α-glucosidase. As stated above, these components may be comprised in a single layer, or may be comprised in different layers. In order to secure the water-permeability of such a reagent layer, the developing reaction layer is preferably a porous layer consisting of a porous medium, or a layer consisting of a hydrophilic polymer binder. Among such water-permeable layers, a continuous layer consisting of a hydrophilic polymer binder is preferable.

When a porous layer is used as such a developing reaction layer, such a porous medium may be either a fibrous medium or a non-fibrous medium. Examples of a fibrous material that can be used herein include a filter, a non-woven fabric, a woven fabric (a plain-woven fabric, for example), a knitted fabric (a tricot knitted fabric, for example), and a glass fiber filter. Examples of a non-fibrous material include: a membrane filter consisting of cellulose acetate and the like described in JP Patent Publication (Kokai) No. 49-53888 A (1974), etc.; and an intercommmunicating pore-containing granulated structure layer consisting of inorganic or organic fine particles described in JP Patent Publication (Kokai) No. 49-53888 A (1974), JP Patent Publication (Kokai) No. 55-90859 A (1980) (the corresponding U.S. Pat. No. 4,258,001), JP Patent Publication (Kokai) No. 58-70163 A (1983) (the corresponding U.S. Pat. No. 4,486,537), etc. Moreover, a laminated product of several porous layers, which have been partially adhered, described in JP Patent Publication (Kokai) No. 61-4959 A (1986) (the corresponding European Patent Publication No. EP0166365A), JP Patent Publication (Kokai) No. 62-116258 A (1987), JP Patent Publication (Kokai) No. 62-138756 A (1987) (the corresponding European Patent Publication No. EP0226465A), JP Patent Publication (Kokai) No. 62-138757 A (1987) (the corresponding European Patent Publication No. EP0226465A), JP Patent Publication (Kokai) No. 62-138758 A (1987) (the corresponding European Patent Publication No. EP0226465A), etc. is also preferable.

Such a porous layer may be a developing layer having, what is called, measuring action, whereby a liquid is developed on an area that is almost proportional to the amount of the liquid to be supplied. As such a developing layer, a woven fabric, a knitted fabric, etc. are preferable. A woven fabric may be subjected to the glow discharge treatment described in JP Patent Publication (Kokai) No. 57-66359 A (1982). In order to control a developing area, a developing rate, etc., such a developing layer may comprise a hydrophilic polymer or a surfactant described in JP Patent Publication (Kokai) No. 60-222770 A (1985) (corresponding to EP0162301A), JP Patent Publication (Kokai) No. 63-219397 A (1988) (the corresponding D.E. Patent Publication No. DE3717913A), JP Patent Publication (Kokai) No. 63-112999 A (1988) (corresponding to DE3717913A), and JP Patent Publication (Kokai) No. 62-182652 A (1987) (corresponding to DE3717913A).

For example, a method, which comprises previously infiltrating a porous membrane or the like consisting of a paper, a fabric, or a polymer with the reagent of the present invention or applying the aforementioned reagent to the porous membrane, and then adhering the porous membrane onto another water-permeable layer established on a supporting medium by the method described in JP Patent Publication (Kokai) No. 55-164356 A (1980), is also useful.

The thickness of the thus produced regent layer is not particularly limited. When such a reagent layer is established as a coating layer, the thickness is appropriately between approximately 1 μm and 50 μm, and preferably between 2 μm and 30 μm. When such a reagent layer is established by a method other than coating, such as lamination, the thickness greatly varies in the range from several tens of μm to several hundreds of μm.

When such a reagent layer is constituted with a water-permeable layer consisting of a hydrophilic polymer binder, examples of a hydrophilic polymer that can be used include: gelatin and a derivative thereof (phthalated gelatin, for example); a cellulose derivative hydroxyethyl cellulose, for example); agarose; sodium alginate; an acrylamide copolymer; a methacrylamide copolymer; a copolymer consisting of acrylamide or methacrylamide and various types of vinyl monomers; polyhydroxyethyl methacrylate; polyvinyl alcohol; polyvinylpyrrolidone; sodium polyacrylate; and a copolymer consisting of acrylic acid and various types of vinyl monomers.

A reagent layer constituted with a hydrophilic polymer binder can be established by applying an aqueous solution or an aqueous dispersion, which comprises a reagent composition comprising a substrate and other components and a hydrophilic polymer, onto a supporting medium or another layer such as a detection layer, and then drying it, according to the method described in JP Patent Publication (Kokoku) No. 53-21677 B (1978) (the corresponding U.S. Pat. No. 3,992,158), JP Patent Publication (Kokai) No. 55-164356 A (1980) (the corresponding U.S. Pat. No. 4,292,272), JP Patent Publication (Kokai) No. 54-101398 A (1979) (the corresponding U.S. Pat. No. 4,132,528), JP Patent Publication (Kokai) No. 61-292063 A (1986) (Chemical Abstracts, 106: 210567y), etc.

The dry thickness of a reagent layer comprising a hydrophilic polymer as a binder is between approximately 2 μm and approximately 50 μm, and preferably between approximately 4 μm and approximately 30 μm. The coated amount is between approximately 2 g/m² and approximately 50 g/m², and preferably between approximately 4 g/m² and approximately 30 g/m².

For the purpose of improving various properties such as coating properties, diffusibility of a diffusive compound, reactivity, and preservative quality, in addition to an oligosaccharide substrate labeled with p-nitrophenol and α-glucosidase, various types of additives including organic products or inorganic products, such as a surfactant, a pH buffer composition, fine powders, or an antioxidant, may be added to the developing reaction layer. An example of a buffer that may be contained in the reagent layer is a pH buffer described in: "*Kagaku Binran, Kiso Hen* (Chemistry Handbook, Basic Edition)" edited by the Chemical Society of Japan, (Tokyo, Maruzen, 1966), pp. 1312-1320; R. M. C. Dawson et al., "Data for Biochemical Research," 2$^{nd}$ edition, (Oxford at the Clarendon Press, 1969), pp. 476-508; "Biochemistry," 5, pp. 467-477 (1966); and "Analytical Biochemistry," 104, pp. 300-310 (1980). Specific examples of such a pH buffer include: a buffer comprising borate; a buffer comprising citric acid or citrate; a buffer comprising glycine; a buffer comprising bicine; a buffer comprising HEPES; and Good's buffer such as a buffer comprising MES.

The dry analysis element that can be used in the present invention can be prepared by the methods described in various specifications such as JP Patent Publication (Kokai) No. 49-53888 A (1974) (the corresponding U.S. Pat. No. 3,992,158), JP Patent Publication (Kokai) No. 51-40191 A (1976) (the corresponding U.S. Pat. No. 4,042,335), JP Patent Publication (Kokai) No. 55-164356 A (1980) (the corresponding U.S. Pat. No. 4,292,272), and JP Patent Publication (Kokai) No. 61-4959 A (1986) (the corresponding EPC Patent Publication No. 0166365A).

From the viewpoint of production, wrapping, transport, conservation, measurement operations, etc., it is preferable that the analysis element that can be used in the present invention be cut into a section such as a square with a side of approximately 10 to approximately 30 mm or a circle with the almost the same size as that of the square, and the thus obtained section be placed in a slide frame described in JP Patent Publication (Kokoku) No. 57-28331 B (1982) (the corresponding U.S. Pat. No. 4,169,751), JP Utility Model Publication (Kokai) No. 56-142454 U (1981) (the corresponding U.S. Pat. No. 4,387,990), JP Patent Publication (Kokai) No. 57-63452 A (1982), JP Utility Model Publication (Kokai) No. 58-32350 U (1983), JP Patent Publication (Kohyo) No. 58-501144 A (1983) (the corresponding International Publication WO83/00391), etc., thereby using the analysis element in the form of a chemical analysis slide. Depending on the purpose of use, the analysis element may have a long tape form, and it may be placed in a cassette or a magazine. Or, a section thereof may be attached to or placed in a card with an opening. Otherwise, the cut section may be directly used.

Using the analysis method of the present invention, the activity of α-amylase as a test substance contained in a liquid sample can be measured. For example, approximately 2 to 30 μl of and preferably 4 to 15 μl of sample (that is, a non-human animal non-diluted sample comprising α-amylase and glucoamylase) is applied onto a reagent layer. The analysis element, onto which the sample has been applied, was incubated at a constant temperature ranging from approximately 20° C. to approximately 45° C., and preferably at a temperature ranging from approximately 30° C. to approximately 40° C., for 1 to 10 minutes. Thereafter, the α-amylase activity can be measured by measuring the level of coloration or discoloration in the analysis element. The amount of a liquid sample applied, the incubation time, and the incubation temperature are kept constant, so that the quantitative analysis can be carried out with high precision.

α-amylase can be quantified as mentioned above. The α-amylase activity calculation time (window) is preferably 5 minutes or less, preferably 1 to 5 minutes. If the starting time of the α-amylase activity calculation time is too early, a precise value may not be obtained due to the effect of interfering substance or the time-lag of measurement start of an automatic analyzer. The effect of interfering substance is not particularly limited, and may include effect of bilirubin, hemolysis hemoglobin, total proteins, sugars (glucose or maltose, for example), or ascorbic acid. On the other hand, if the stopping time of the α-amylase activity calculation time is too late, oligosaccharide substrate labeled with p-nitrophenol is consumed especially in a sample of high α-amylase activity, and the difference of OD changes become small, and thus precise value may not be obtained.

Preferably, the dry analysis element of the present invention is measured by using automatic analyzer, and quantification analysis can be carried out with high accuracy. An automatic analyzer such as FUJI DRI-CHEM Analyzer FDC-7000, FDC-3500, FDC-5500 or FDC-4000 of FUJIFILM Corporation can be used as an automatic analyzer.

The present invention will be more specifically described in the following examples. However, these examples are not intended to limit the scope of the present invention.

EXAMPLES

Comparative Example 1

(1) Measurement with Dry Analysis Element Used in Measurement of Human Sample
Production of Coloring Layer:

A coating solution was applied in the following amount onto a polyethylene terephthalate colorless, transparent and smooth film having a thickness of 180 μm, which had previously been coated with gelatin. Thereafter, it was dried.

| | |
|---|---|
| Gelatin | 14 g/m$^2$ |
| HEPES | 0.8 g/m$^2$ |
| Surfactant 10G | 0.3 g/m$^2$ |
| Poly-co-(styrene-methylmorpholiniummethylstyrene-divinylbenzene (polymerization ratio = 55:43:2) (15% latex solution) | 28 g/m$^2$ |

Herein, the coating solution was adjusted to pH 6.5 by addition of a dilute NaOH solution.
HEPES indicates N-2-hydroxyethylpiperazine-N'-ethanesulfonic acid.
Surfactant 10G indicates poly-oxy(2-hydroxy)propylenenonylphenylether (manufactured by Olin Corp.)

Production of Developing Reaction Layer:

Subsequently, water was uniformly supplied to the aforementioned gelatin layer at a ratio of approximately 30 g/m$^2$, so that the water could be infiltrated into the aforementioned layer. A tricot knitted fabric produced by knitting at 36 gages an approximately 50-denier spun yarn of polyethylene terephthalate was lightly pressed and laminated on the gelatin layer, followed by drying. Thereafter, a reagent solution was applied in the following amount onto the aforementioned fabric, and it was then dried.

| | |
|---|---|
| Polyvinylpyrrolidone | 5 g/m$^2$ |
| HEPES | 6 g/m$^2$ |
| Surfactant 10G | 1 g/m$^2$ |
| p-nitrophenyl-α-D-maltopentaoside | 2 g/m$^2$ |

Herein, the coating solution was adjusted to pH 7.3 by addition of a dilute NaOH solution. Furthermore, another reagent solution was applied in the following amount onto the aforementioned fabric, and it was then dried.

| | |
|---|---|
| Polyvinylpyrrolidone | 3 g/m$^2$ |
| HEPES | 1 g/m$^2$ |
| Surfactant 10G | 1 g/m$^2$ |
| α-glucosidase | 100 KU/m$^2$ |

Herein, the coating solution was adjusted to pH 7.3 by addition of a dilute NaOH solution.

The aforementioned integral-type multilayer analysis element was cut into a chip with a size of 12 mm×13 mm, and the obtained chip was then placed in a slide flame (described in JP Patent Publication (Kokai) No. 57-63452 A (1982)), so as to produce a dry analysis element used in the analysis of α-amylase.

(2) Measurement of Canine Sample

A 3 times dilution of a canine sample was made in normal saline, and it was then measured with the dry analysis element produced in Comparative example 1 (1). The measurable range of a method using this dry analysis element was up to 1200 U/L. Thus, in the case of canine samples, many of which contained a high level of amylase, it was necessary to dilute half or more of the samples. Accordingly, in the present experiment, all samples were 3 times diluted before measurement. The results are shown in FIG. 1. In the reference process, L-type Wako amylase, in vitro diagnosis reagent of Wako Pure Chemical Industries, Ltd.

In Comparative example 1, a dilution operation was required, and a poor correlation was obtained using such canine samples.

Example 1

Measurement with Dry Analysis Element Used in Measurement of Canine Sample (1) Production of Dry Analysis Element Used in Measurement of Canine Sample Amylase
Production of Coloring Layer:

An aqueous solution (pH 6.5) was applied in the following amount onto a polyethylene terephthalate colorless, transparent and smooth film having a thickness of 180 μm, which had previously been coated with gelatin. Thereafter, it was dried.

| | |
|---|---|
| Gelatin | 14 g/m$^2$ |
| HEPES | 0.8 g/m$^2$ |
| Surfactant 10G | 0.3 g/m$^2$ |
| Poly-co-(styrene-methylmorpholiniummethylstyrene-divinylbenzene (polymerization ratio = 55:43:2) (15% latex solution) | 28 g/m$^2$ |

Herein, the coating solution was adjusted to pH 6.5 by addition of a dilute NaOH solution.

Production of Developing Reaction Layer:

Subsequently, water was supplied to the aforementioned gelatin layer as a whole at a ratio of approximately 30 g/m$^2$, so that the water could be infiltrated into the aforementioned layer. A tricot knitted fabric produced by knitting at 36 gages an approximately 50-denier spun yarn of polyethylene terephthalate was lightly pressed and laminated on the gelatin layer, followed by drying. Thereafter, a reagent solution (pH 6.5) was applied in the following amount onto the aforementioned fabric, and it was then dried.

| | |
|---|---|
| Polyvinylpyrrolidone | 4.3 g/m$^2$ |
| HEPES | 6.4 g/m$^2$ |
| Surfactant 10G | 1.7 g/m$^2$ |
| BG7-PNP | 2.7 g/m$^2$ |

Herein, the coating solution was adjusted to pH 6.5 by addition of a dilute HCl solution or a dilute NaOH solution.
BG7-PNP is 4,6-ethylidene-4-nitrophenyl-α-D-maltoheptaoside.

Furthermore, another reagent solution was applied in the following amount onto the aforementioned fabric, and it was then dried.

| | |
|---|---|
| Polyvinylpyrrolidone | 2.7 g/m$^2$ |
| HEPES | 1.7 g/m$^2$ |
| Surfactant 10G | 1.0 g/m$^2$ |
| α-glucosidase | 100 KU/m$^2$ |

Herein, the coating solution was adjusted to pH 6.5 by addition of a dilute HCl solution or a dilute NaOH solution.

The aforementioned integral-type multilayer analysis element was cut into a chip with a size of 12 mm×13 mm, and the obtained chip was then placed in a slide flame (described in JP Patent Publication (Kokai) No. 57-63452 A (1982)), so as to produce a dry analysis element used in the analysis of α-amylase.

(2) Measurement of Canine Serum Amylase (Comparison Regarding Correlation Among Multiple Samples, Measurement Range, and Window)

Figure 2:
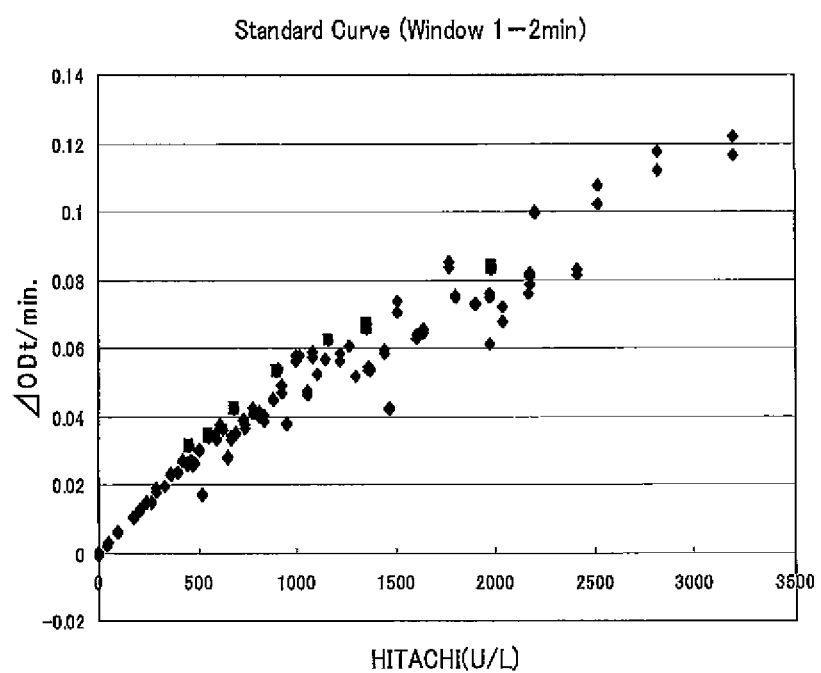
FIG. 2 shows the results obtained by measuring a non-diluted canine sample using the dry analysis element produced in Example 1 (1).
Figure 3:
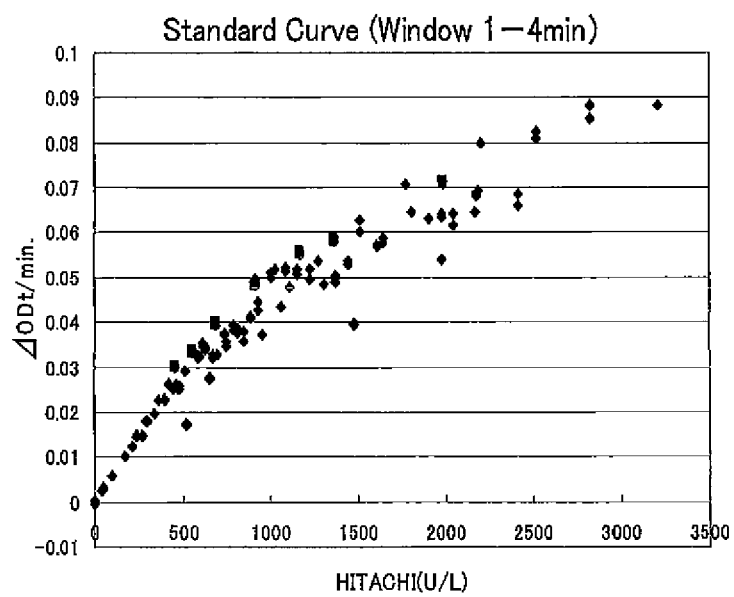
FIG. 3 also shows the results obtained by measuring a non-diluted canine sample using the dry analysis element produced in Example 1 (1).

10 μl of non-diluted canine serum was applied to the dry analysis produced in Example 1 (1), and it was then incubated at 37° C. Thereafter, the reflection OD at 400 nm was measured. ODr was converted to ODt, and an activity calculation time (window) was then selected from among 1 to 4 minutes. Each calibration curve was produced, and a measurable range was then obtained from such calibration curve. Representative examples of such calibration curves are shown in FIGS. 2 and 3. Measurement ranges obtained from such calibration curves are shown in Table 1.

TABLE 1

Measurement of canine serum amylase using analysis element of the present invention

| Experiment | Window (min) | Upper limit of measurement range (U/L) |
|---|---|---|
| 2-1 | 1 to 2 | Approximately 2500 |
| 2-2 | 1 to 3 | Approximately 2300 |
| 2-3 | 1 to 4 | Approximately 2100 |
| 2-4 | 2 to 3 | Approximately 2000 |
| 2-5 | 2 to 4 | Approximately 1800 |

These results demonstrated that when the method for measuring a canine sample using the dry analysis element described in Example 1 (1) was compared with the method for measuring a canine sample using the dry analysis element described in the comparative example, a correlation among multiple samples was significantly improved, the measurement range in the case of the measurement without dilutions was significantly increased, and such a measurement range could be controlled by changing the measurement window, and when the measurement was carried out after 1 minute to 2 minutes, the measurement range up to 2500 U/L could be quantified without dilutions.

As described above, when a canine sample was measured using a dry analysis element (reaction pH: 6.5), it was found that it could be quantified even though the optimal pH was shifted. Moreover, the measurement range was expanded, and almost all samples could be measured without dilutions. Thus, it was found that burden on users was significantly reduced.

Example 2

(1) Production of Dry Analysis Element Used in Measurement of Canine Sample Amylase A dry analysis element for measurement of α-amylase was produced in the same way as in Example 1, except that pH of the reagent layers (coloring layer and/or developing reaction layer) was changed as shown in Table 2 by using a dilute NaOH solution or a dilute HCl solution.

TABLE 2

| Dry Analysis Element | pH of the reagent layer | Remark |
|---|---|---|
| 3-1 | 5.0 | Comparative |
| 3-2 | 6.0 | Invention |
| 3-3 | 6.5 | Invention (=Example 1(1)) |
| 3-4 | 7.0 | Comparative |

(2) Measurement of Canine Serum Amylase

The dry analysis elements produced in Example 2 (1) were placed in FUJI DRI-CHEM Analyzer FDC-7000, and 10 μl of non-diluted canine serum (amylase activity was 2450 U/L when measured by the reference process) was applied thereto, and it was then incubated at 37° C. Thereafter, the reflection OD at 400 nm was measured. ODr was converted to ODt, and an activity calculation time (window) was then set to be 1.5 to 3 minutes. Calibration curves in each dry analysis element were produced. The amylase activity in measurement range and the CV value were examined.

In the reference process in the preparation of calibration curves, pancreas-related reagent series "RD" Liquitec AMY EPS of Loche Diagnositic Inc, was used.

Figure 4:
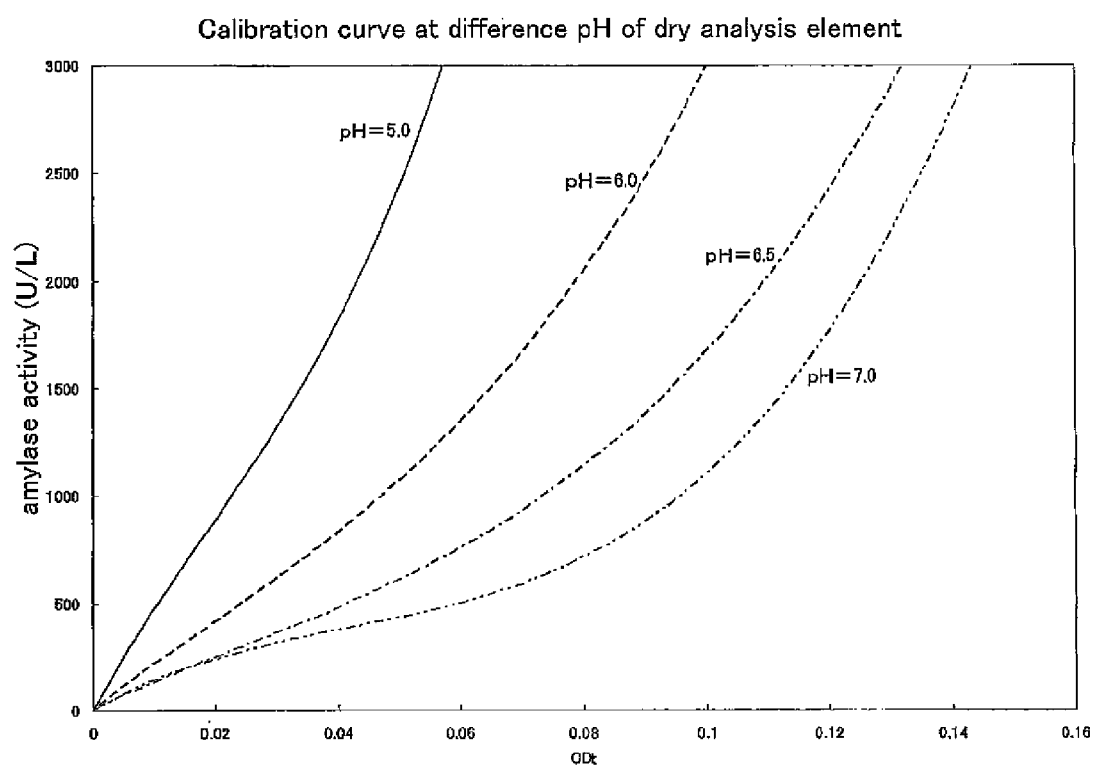
FIG. 4 shows the calibration curve in the measurement of canine serum amylase in Example 2.

Representative example of such calibration curves is shown in FIG. 4. Amylase activity and CV value are shown in Table 3.

TABLE 3

Canine α-amylase activity using the dry analysis elements of the present invention

| Experiment | Optical density ODr of amylase activity 2450 U/L in reference process | Amylase Activity (U/L) | CV value (%) at the left amylase activity | Remark |
|---|---|---|---|---|
| 3-1 | 0.68 | 2490 | 2.0 | Comparative |
| 3-2 | 0.90 | 2420 | 3.0 | Invention |
| 3-3 | 1.10 | 2370 | 2.6 | Invention |
| 3-4 | 1.23 | 2560 | 5.5 | Comparative |

The permissible level of CV value is "5% or less". The permissible level of optical density (ODr)) is "0.8 or more".

The permissible level of Amylase Activity of the dry elements is "±15% of that in reference process (ie. 2082~2817 U/L)".

As is understood from these results, it was demonstrated that sufficient optical density can be obtained and good CV value can be obtained by measuring canine sample using the dry analysis element 3-2 or 3-3 of Example 2 (1).

On the other hand, in the dry analysis element 3-1 of comparative example, CV value is permissible, but sufficient optical density could not be obtained even in a sample of high amylase activity, and specificity could not be obtained over all regions. In the dry analysis element 3-4 of comparative example, sufficient optical density could be obtained, but the CV value became worse.

As mentioned above, advantageous effects of interest were achieved in the scope of the present invention.

By using cat sample in place of canine sample, evaluation was carried out in the same way as in the above. The results are shown in Table 4. Good results were obtained in cat sample in the same way as in canine sample.

TABLE 4

Cat α-Amylase activity using the dry analysis elements of the present invention

| Experiment | Optical density ODr of amylase activity 2078 U/L in reference process | Amylase Activity (U/L) | CV value (%) at the left amylase activity | Remark |
|---|---|---|---|---|
| 3-5 | 0.74 | 3977 | 4.3 | Comparative |
| 3-6 | 0.84 | 2167 | 2.8 | Invention |
| 3-7 | 0.89 | 2104 | 2.7 | Invention |
| 3-8 | 0.98 | 1606 | 5.5 | Comparative |

Example 3

The dry analysis element 3-3 produced in Example 2 (1) was used, and FUJI DRI-CHEM Analyzer FDC-4000 was used. 10 µl of non-diluted canine serum was applied thereto, and it was then incubated at 37° C. Thereafter, the reflection OD at 400 nm was measured. ODr was converted to ODt, and an activity calculation time (window) was then set to be 1 to 3 minutes or 1.5 to 3 minutes. Calibration curves in each dry analysis element were produced. The amylase activity in measurement range and the CV value were examined.

In the reference process in the preparation of calibration curves, pancreas-related reagent series "RD" Liquitec AMY EPS of Loche Diagnositic Inc, was used.

Figure 5:
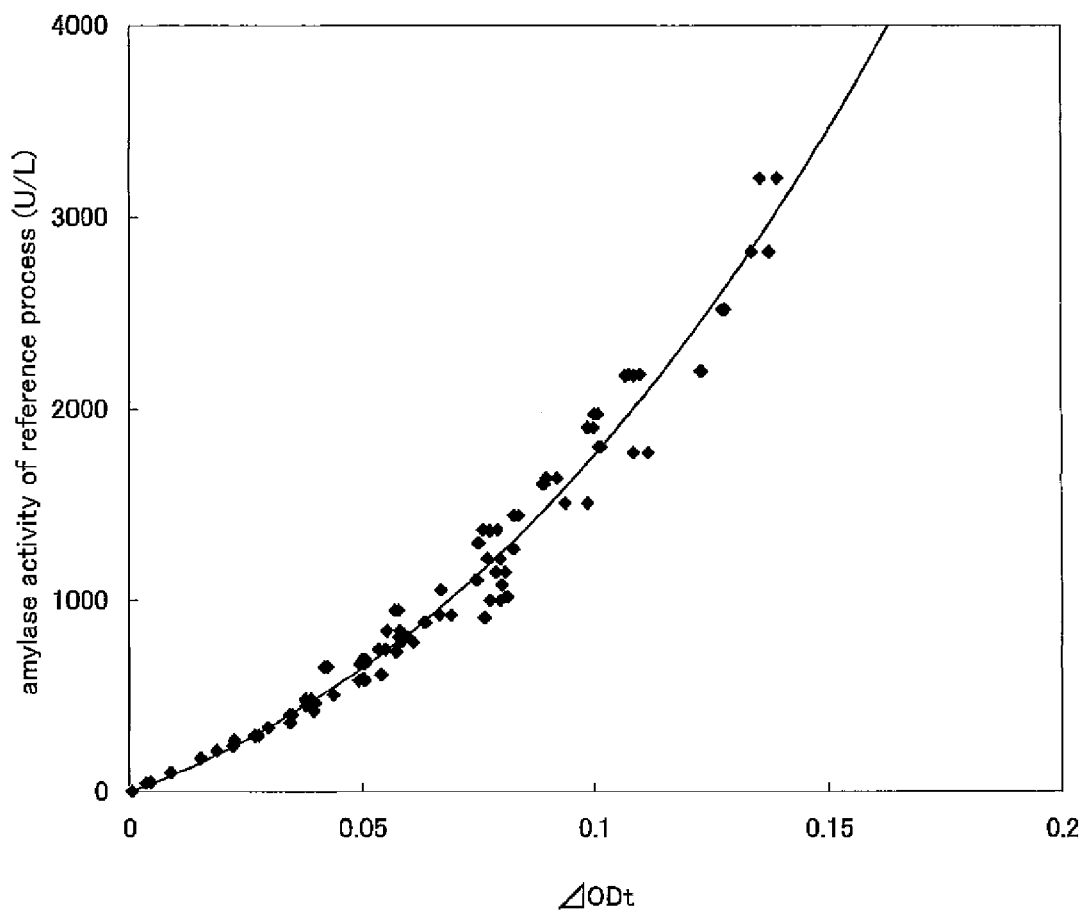
FIG. 5 shows the calibration curve in the measurement of canine serum amylase in Example 3.

Representative example of such calibration curves (activity calculation time (window): 1.5 to 3 minutes) is shown in FIG. 5. Amylase activity and CV value are shown in Table 5.

TABLE 5

Canine α-amylase activity using the dry analysis elements of the present invention

| Experiment | WINDOW | Amylase Activity (U/L) and CV value (%) | Amylase Activity (U/L) and CV value (%) | Remark |
|---|---|---|---|---|
| 4-1 | 1-3 | 1245, 3.3 | 2126, 3.5 | Invention |
| 4-2 | 1.5-3 | 1228, 3.5 | 2159, 3.9 | Invention |
| Amylase activity (U/L) in reference process | | 1299 | 2180 | Reference |

The permissible level of CV value is "5% or less".

The permissible level of Amylase Activity of the dry elements is "±15% of that in reference process (ie. 1104~1494 U/L, 1853~2057 U/L, respectively)".
As is understood from these results, it was demonstrated that good CV value can be obtained by measuring canine sample using the dry analysis element 3-3 of the present invention and WINDOW region. As mentioned above, advantageous effects of interest were achieved in the scope of the present invention.

By using cat sample in place of canine sample, evaluation was carried out in the same way as in the above. The results are shown in Table 6. Good results were obtained in cat sample in the same way as in canine sample.

TABLE 6

Cat α-amylase activity using the day analysis elements of the present invention

| Experiment | WINDOW | Amylase Activity (U/L) CV value (%) | Amylase Activity (U/L) and and CV value (%) | Remark |
|---|---|---|---|---|
| 4-3 | 1-3 | 1125, 2.7 | 2150, 1.8 | Invention |
| 4-4 | 1.5-3 | 1070, 2.8 | 2104, 2.7 | Invention |
| Amylase activity (U/L) in reference process | | 1016 | 2078 | Reference |

The invention claimed is:

1. A method for specifically measuring α-amylase contained in a non-human animal sample comprising α-amylase and glucoamylase without diluting said sample,
   which method comprises a reaction of decomposing an oligosaccharide having a protected nonreducing terminus and a p-nitrophenyl group at the reducing terminus thereof by the α-amylase in said sample by applying an undiluted non-human animal sample to a dry analysis element comprising the oligosaccharide and a mordant on an identical or different reagent layer thereof; and
   a reaction of decomposing the thus obtained product by α-glucosidase, wherein
   pH of the reactions is 6 to 6.5;
   the non-human animal sample is a canine sample or a cat sample, and
   the oligosaccharide having a protected nonreducing terminus and a p-nitrophenyl group at the reducing terminus thereof is 4,6-ethylidene-4-nitrophenyl-α-D-maltoheptaoside, and the α-amylase activity is calculated from the time of 1 to 2 minutes after the application of the undiluted non-human animal sample to the dry analysis element to the time of 2 to 4 minutes after said application.

2. The method of claim 1 wherein the measurement is carried out by using a dry analysis element comprising an oligosaccharide having a protected nonreducing terminus and a p-nitrophenyl group at the reducing terminus thereof and a mordant on an identical or different reagent layer(s) thereof.

3. The method of claim 2 wherein the mordant is an organic polymer comprising a quaternary ammonium salt.

4. The method of claim 2 wherein the mordant is a latex consisting of poly-co-(styrene-methylmorpholiniummethylstyrene-divinylbenzene).

5. The method of claim 2 wherein the α-amylase activity calculation time (window) is 5 minutes or less.

6. The method of claim 2 wherein the α-amylase activity calculation time (window) is 1 to 5 minutes.

* * * * *